US012420076B2

(12) United States Patent
Spanier et al.

(10) Patent No.: US 12,420,076 B2
(45) Date of Patent: Sep. 23, 2025

(54) INTRAVASCULAR BLOOD PUMP WITH OUTFLOW HOSE

(71) Applicant: Abiomed, Inc., Danvers, MA (US)

(72) Inventors: Gerd Spanier, Aachen (DE); Zhongwei Qi, Andover, MA (US); Thorsten Siess, Aachen (DE); Frank Kirchhoff, Aachen (DE)

(73) Assignee: Abiomed, Inc., Danvers, MA (US)

( * ) Notice: Subject to any disclaimer, the term of this patent is extended or adjusted under 35 U.S.C. 154(b) by 396 days.

(21) Appl. No.: 17/147,711

(22) Filed: Jan. 13, 2021

(65) Prior Publication Data

US 2021/0213273 A1 Jul. 15, 2021

Related U.S. Application Data

(60) Provisional application No. 62/961,017, filed on Jan. 14, 2020.

(51) Int. Cl.
*A61M 60/165* (2021.01)
*A61M 60/135* (2021.01)
*A61M 60/216* (2021.01)

(52) U.S. Cl.
CPC ........ *A61M 60/135* (2021.01); *A61M 60/216* (2021.01); *A61M 2205/04* (2013.01);
(Continued)

(58) Field of Classification Search
CPC .. A61M 60/148; A61M 60/13; A61M 60/422; A61M 60/216
See application file for complete search history.

(56) References Cited

U.S. PATENT DOCUMENTS 8,439,859 B2 5/2013 Pfeffer et al.
10,238,783 B2 3/2019 Aboul-Hosn et al.
(Continued)

FOREIGN PATENT DOCUMENTS

AU 2013254682 A1 11/2014
EP 3205359 A1 8/2017
(Continued)

OTHER PUBLICATIONS

International Search Report and Written Opinion for corresponding International Application No. PCT/US2021/013153 dated Mar. 26, 2021 (12 pages).
(Continued)

*Primary Examiner* — Michael J D'Abreu
(74) *Attorney, Agent, or Firm* — BOTOS CHURCHILL IP LAW LLP

(57) ABSTRACT

An intravascular blood pump includes a pump housing having an input port and an output port. A relatively short intake cannula may draw blood in through an intake port and deliver the blood to the input port of the pump housing. The intake cannula is relatively short, to prevent excess hydraulic loss. An outflow hose is connected to the output port of the pump housing, so as to convey blood exiting the output port through the outflow hose in a downstream direction to a discharge port, e.g. into an aorta or other blood vessel. Despite the short intake cannula, the outflow hose longitudinally separates the intake port from the discharge port sufficiently so the intake port and the discharge port remain on opposite sides of a heart valve, despite inadvertent longitudinal shifts of the intravascular heart pump.

26 Claims, 12 Drawing Sheets

(52) U.S. Cl.
CPC .............. *A61M 2205/103* (2013.01); *A61M 2205/3331* (2013.01)

(56) References Cited

U.S. PATENT DOCUMENTS

| | | | |
|---|---|---|---|
| 2004/0044266 A1 | 3/2004 | Siess et al. | |
| 2008/0103591 A1* | 5/2008 | Siess ................... | A61M 60/422 623/3.13 |
| 2013/0060077 A1 | 3/2013 | Liebing | |
| 2016/0303299 A1 | 10/2016 | Muller | |
| 2017/0290967 A1* | 10/2017 | Botterbusch ........ | A61M 60/148 |
| 2018/0064860 A1* | 3/2018 | Nunez ................. | A61M 60/816 |
| 2019/0046702 A1 | 2/2019 | Siess et al. | |
| 2019/0321530 A1 | 10/2019 | Cambronne et al. | |

FOREIGN PATENT DOCUMENTS

| | | | |
|---|---|---|---|
| JP | 2019504720 A | 2/2019 | |
| JP | 2019508128 A | 3/2019 | |
| WO | WO-2005123158 A1 * | 12/2005 | .......... A61M 1/3653 |
| WO | 2006051023 A1 | 5/2006 | |
| WO | 2017137578 A1 | 8/2017 | |
| WO | 2018226991 A1 | 12/2018 | |
| WO | 2020003110 A2 | 1/2020 | |

OTHER PUBLICATIONS

Office Action with Search Report issued in Application CN202180016768.6 dated Aug. 12, 2024 (20 pp.).
TIPO Search Report issued in corresponding Taiwanese Patent Application No. 110101222, mailed Feb. 25, 2024, 3 pages.
Office Action issued in corresponding Israeli Patent Application No. 294473, mailed Dec. 26, 2024, 4 pages.
Office Action dated Oct. 28, 2024 for Japanese Patent Application No. 2022-542900 (14 pp.).
Second Office Action issued in corresponding Chinese Patent Application No. 202180016768.6, dated May 16, 2025 (12 pp.).

* cited by examiner

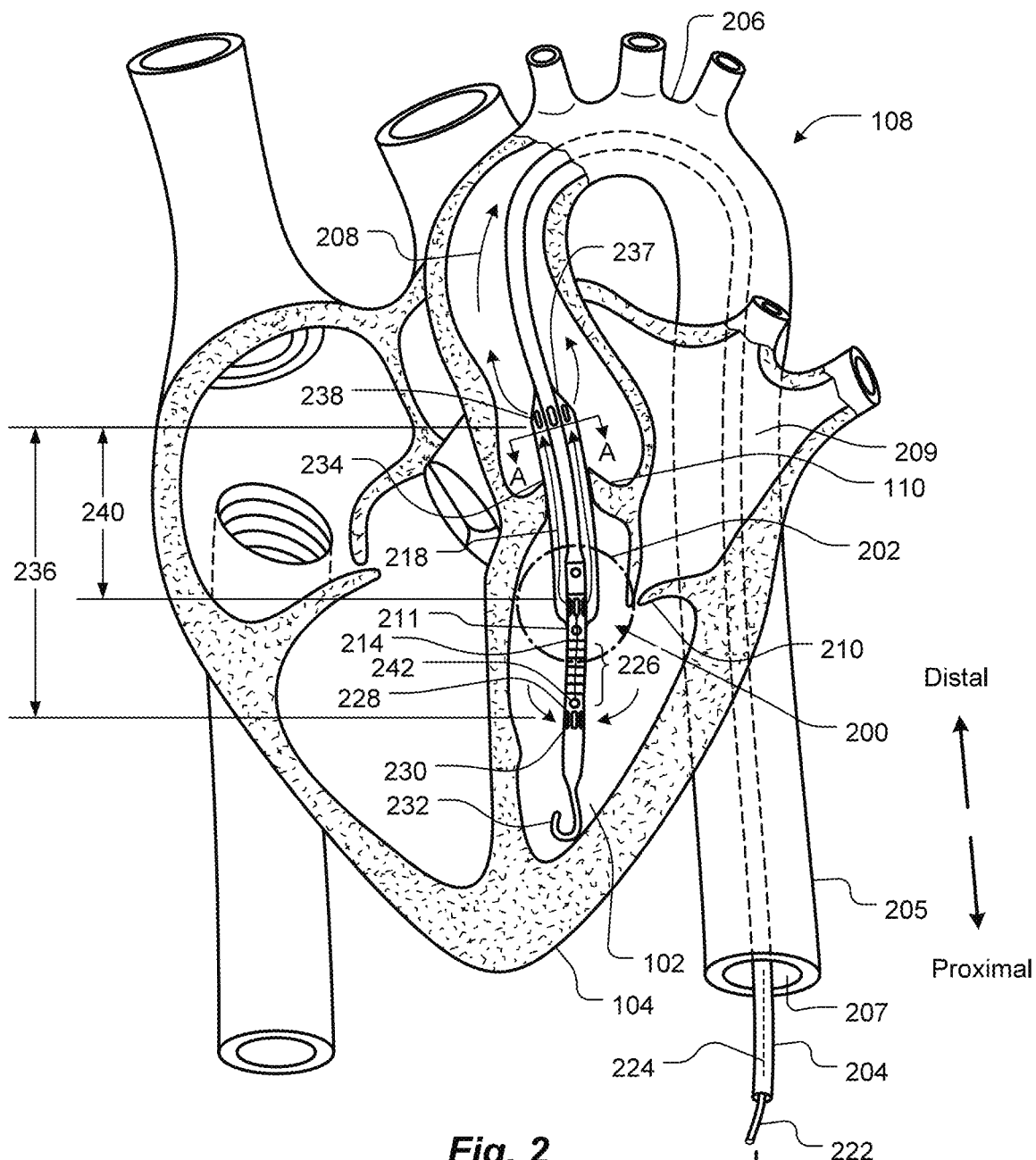
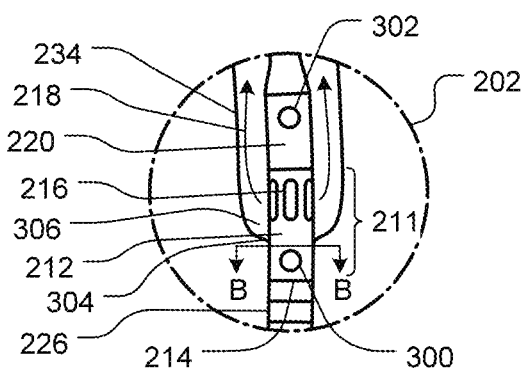 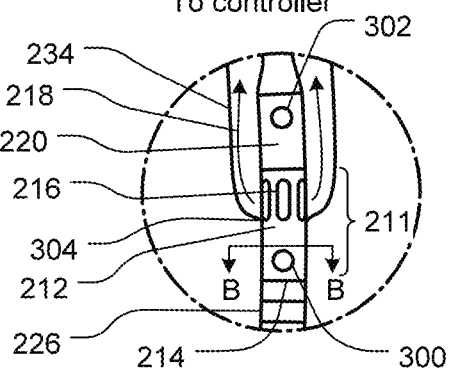
Fig. 2
Fig. 3a    Fig. 3b

Section A

Section B

INTRAVASCULAR BLOOD PUMP WITH OUTFLOW HOSE

CROSS-REFERENCE TO RELATED APPLICATIONS

This application claims the benefit of U.S. Provisional Patent Application No. 62/961,017, filed 14 Jan. 2020, titled "Intravascular Blood Pump with Outflow Hose," the entire contents of which are hereby incorporated by reference herein, for all purposes.

BACKGROUND

Technical Field

The present invention relates to intravascular blood pumps and, in particular, to intravascular blood pumps having outflow hoses that increase longitudinal spacing between blood intake ports and blood discharge ports.

Related Art

An intravascular blood pump is a pump that can be advanced through a patient's blood circulatory system, i.e., veins and/or arteries, to a position in the patient's heart or elsewhere within the patient's circulatory system. For example, an intravascular blood pump may be inserted via a catheter and positioned to span a heart valve. The intravascular blood pump is typically disposed at the end of the catheter. Once in position, the pump may be used to pump blood through the circulatory system and, therefore, temporarily reduce workload on the patient's heart, such as to enable the heart to recover after a heart attack.

Well-known types of intravascular blood pumps include: axial blood pumps, centrifugal, i.e. radial, blood pumps and mixed-type blood pumps, in which blood flow is caused by a combination of axial and radial forces. A blood pump typically includes a pump housing that defines an input port and an output port. An intake cannula extends from the input port of the pump housing to a blood intake port at a distal end of the intake cannula. An impeller is disposed within the pump housing. The impeller may be driven by an electric motor that is also disposed within the pump housing. Alternatively, the impeller may be driven by an external motor, via a flexible drive shaft that extends through the catheter to outside the patient's body. In either case, rotation of the impeller causes blood to be drawn into the blood intake port, flow through the cannula and be expelled from the outlet port of the pump housing.

Some intravascular blood pumps have diametrically-expandable pump housings and diametrically-expandable impellers, whereas other blood pumps have non-expandable, that is fixed-diameter, pump housings and non-expandable, that is fixed-diameter, impellers. An expandable-housing blood pump is inserted into a patient while the blood pump and impeller are in compressed (non-expanded) states, and then after the blood pump is properly positioned, the pump housing and the impeller are expanded in diameter. The compressed state makes an expandable-housing blood pump typically easier to introduce and guide through the patient's vasculature than a fixed-diameter blood pump.

In general, once expanded, impellers in expandable-housing blood pumps are larger in diameter, and can therefore operate at lower revolutionary speeds to pump at equivalent flow rates, than fixed-diameter blood pumps. These lower speeds enable the expandable-housing pumps to be driven by flexible drive shafts and external motors. In contrast, fixed-diameter blood pumps currently must be driven by motors disposed close to the impellers. Such internal motors are powered by electric wires that extend through the catheter to an external power supply. Internal motors must be smaller, and spin faster, than external motors, making the internal motors more complex and expensive than the external motors. Nevertheless, most intravascular blood pumps in use today are non-expandable blood pumps with internal motors.

An exemplary expandable-housing blood pump is described in U.S. Pat. No. 8,439,859, and an exemplary fixed-diameter blood pump is described in U.S. Pat. Publ. No. 2019/0046702, the entire contents of each of which are hereby incorporated by reference herein, for all purposes.

When disposed in an operating position, the blood intake port of an intravascular blood pump is typically upstream of the blood output port. When a blood pump is positioned to span a heart valve, leaves of the heart valve open and close over the blood pump. That is, the leaves close around the blood pump. Thus, in use, the pump body extends across the heart valve, and in the closed position, the leaves of the heart valve physically capture, and seal around, the body of the blood pump.

A catheter and blood pump may inadvertently shift for various reasons, such as due to patient movement or heart action. However, for a blood pump that is disposed across a heart valve, it is important that the blood intake port remains on one side of the heart valve and the blood output port remains on the other side of the heart valve. If the blood pump were to shift along the longitudinal axis of the catheter, such that both the blood intake port and the blood output port were on the same side of the heart valve, efficiency of the blood pump would be severely negatively impacted. Even a relatively small shift of the blood pump that displaces the blood output port to within the heart valve would be problematic, because the heart valve would then close on the blood output port. Although the blood pump may remain effective and pump blood, the pumped blood would be subject to hemolysis.

Increasing the intake cannula's length would further separate the blood intake port from the blood output port and therefore allow for more longitudinal shifting of the blood pump, thereby reducing risk of the negative consequences described above. However, a longer intake cannula would exhibit increased hydraulic loss. To mitigate this increased hydraulic loss, an intake portion of the cannula could be configured to expand in diameter, once the blood pump has been positioned. Such an expandable intake cannula is described in U.S. Pat. Publ. No. 2004/044266 A1, the entire contents of which are hereby incorporated by reference herein, for all purposes. However, such an expandable intake cannula increases complexity and cost of the blood pump and its insertion process. Furthermore, as noted, most vascular blood pumps in use today are non-expandable blood pumps. There is, therefore, a need for a fixed-diameter intravascular blood pump that is more tolerant of longitudinal shifts than prior art blood pumps. Thus, a technical problem is increasing tolerance of a fixed-diameter intravascular blood pump to longitudinal shifts, without increasing intake cannula length.

SUMMARY OF EMBODIMENTS

An embodiment of the present invention provides an intravascular blood pump 200 that includes a catheter 204, a pump housing 211, an impeller 212 and an outflow hose 234. The catheter 204 is configured for insertion into a blood vessel 205. The blood vessel 205 defines an interior volume 207, through which blood flows in a blood flow direction 208. The pump housing 211 is attached to the catheter 204. The pump housing 211 defines an input port 214 and an output port 216. The impeller 212 is disposed within the pump housing 211. The impeller 212 is configured, when rotating, to pump blood from the input port 214 to the output port 216. The outflow hose 234 is in fluid communication with the output port 216 of the pump housing 211. The outflow hose 234 defines a discharge port 238. The discharge port 238 is longitudinally spaced apart 240, in a downstream direction relative to the blood flow direction 208, from the output port 216 of the pump housing 211. The discharge port 238 is in fluid communication with the interior volume 207 of the blood vessel 205.

Optionally, in any embodiment, the outflow hose 234 may be coaxial with the catheter 204.

Optionally, in any embodiment, effective inside cross-sectional area 502 of the outflow hose 234 may be at least as large as effective inside cross-sectional area 700 of the input port 214 of the pump housing 211.

Optionally, in any embodiment, effective inside cross-sectional area 502 of the outflow hose 234 may be greater than effective inside cross-sectional area 700 of the input port 214 of the pump housing 211.

Optionally, in any embodiment, effective inside cross-sectional area 502 of the outflow hose 234 may be at least two times effective inside cross-sectional area 700 of the input port 214 of the pump housing 211.

Optionally, in any embodiment, effective inside cross-sectional area 502 of the outflow hose 234 may be greater than effective inside cross-sectional area 502 of the pump housing 211.

Optionally, in any embodiment, the discharge port 238 of the outflow hose 234 may be longitudinally spaced apart 240, in a downstream direction relative to the blood flow direction 208, from the output port 216 of the pump housing 211 by at least about 50 mm.

Optionally, in any embodiment, the discharge port 238 of the outflow hose 234 may be longitudinally spaced apart 240, in a downstream direction relative to the blood flow direction 208, from the output port 216 of the pump housing 211 by at least about 80 mm.

Optionally, in any embodiment, the discharge port 238 of the outflow hose 234 may be longitudinally spaced apart 240, in a downstream direction relative to the blood flow direction 208, from the output port 216 of the pump housing 211 by at least about 100 mm.

Optionally, in any embodiment, the discharge port 238 of the outflow hose 234 may be longitudinally spaced apart 240, in a downstream direction relative to the blood flow direction 208, from the output port 216 of the pump housing 211 by about 50-150 mm.

Optionally, in any embodiment, the discharge port 238 of the outflow hose 234 may be longitudinally spaced apart 240, in a downstream direction relative to the blood flow direction 208, from the output port 216 of the pump housing 211 by about 80-120 mm.

Optionally, in any embodiment, the outflow hose 234 may be at least about 50 mm long.

Optionally, in any embodiment, the outflow hose 234 may be at least about 80 mm long.

Optionally, in any embodiment, the outflow hose 234 may be at least about 100 mm long.

Optionally, in any embodiment, the outflow hose 234 may be at between about 50 mm long and about 150 mm long.

Optionally, in any embodiment, the outflow hose 234 may be at between about 80 mm long and about 120 mm long.

Optionally, in any embodiment, the outflow hose 234 may be radially collapsible 600 and/or radially expandable 500. The outflow hose 234 may be configured to increase in radius at least about 25% from an initial radius in response to blood pressure generated by the impeller 212, when the impeller 212 pumps blood. The outflow hose 234 may be configured to at least partially collapse 600 for lack of blood pressure, when the impeller 212 pumps no blood.

Optionally, any embodiment may include a first pressure sensor 300 disposed on the pump housing 211, outside the outflow hose 234.

Optionally, any embodiment may include a second pressure sensor 302 disposed inside the outflow hose 234.

Optionally, in any embodiment, the output port 216 of the pump housing 211 may include a plurality of apertures defined circumferentially around the pump housing 211.

Optionally, in any embodiment, the output port 216 of the pump housing 211 may include a plurality of apertures. The plurality of apertures may be defined along a plurality of rows 1600-1604. The rows 1600-1604 may be spaced apart longitudinally along the outflow hose 234.

Optionally, in any embodiment, the input port 214 of the pump housing 211 may include a cannula 226. The cannula 226 may extend longitudinally in an upstream direction, relative to the blood flow direction 208, to an intake port 228 defined by the cannula 226. The intake port 228 may be in fluid communication with the interior volume 207 of the blood vessel 205.

Optionally, in any embodiment, a portion 400 of the cannula 226 that defines the intake port 228 may be radially expandable to a diameter larger than an outside diameter of the pump housing 211.

Optionally, in any embodiment, the cannula 226 may define an intake port 230, and the discharge port 238 of the outflow hose 234 may be longitudinally spaced apart 236, in a downstream direction relative to the blood flow direction 208, from the intake port 230 of the cannula 226 by at least about 90 mm, or at least about 100 mm.

Optionally, any embodiment may include an electric motor 220 disposed in the pump housing 211. The electric motor 220 may be mechanically coupled to the impeller 212 and configured to rotate the impeller 212.

Optionally, any embodiment may include a drive shaft 224 disposed in the catheter 204. The drive shaft 224 may be mechanically coupled to the impeller 212 and configured to transfer rotational energy to the impeller 212 from a motor external to the intravascular blood pump 200.

BRIEF DESCRIPTION OF THE DRAWINGS

The foregoing summary and the invention will be more fully understood by referring to the following Detailed Description of Specific Embodiments in conjunction with the Drawings. The scope of the disclosure is not, however, limited to the specific embodiments disclosed herein. In the drawings:

FIG. 2 shows an intravascular blood pump according to an embodiment of the present invention placed in a left ventricle of a human heart.

FIG. 3a is an enlarged view of a portion of FIG. 2.

FIG. 3*b* is an enlarged view of a portion of FIG. 2, according to alternative embodiment of the present invention.

DETAILED DESCRIPTION OF SPECIFIC EMBODIMENTS

Embodiments of the present invention provide fixed-diameter (non-expandable) intravascular blood pumps that are tolerant of longitudinal shifts along their respective catheters, without lengthening intake cannulas or incurring consequential increased hydraulic losses. Intravascular blood pumps according to the present invention reduce the risk of inadvertently displacing both a blood intake port and a blood output port to the same side of a heart valve. Furthermore, intravascular blood pumps according to the present invention reduce risk of inadvertently displacing the blood output port to a position within the heart valve. Each such intravascular blood pump includes an outflow hose. The outflow hose provides a blood discharge port that is longitudinally separated, in a downstream direction, from the pump output port. The outflow hose longitudinally separates the blood discharge port from the blood intake port more than in prior art blood pumps, without lengthening the intake cannula. In some embodiments, the intake cannula is shorter than in the prior art.

Prior Art Intravascular Blood Pump

Figure 1:
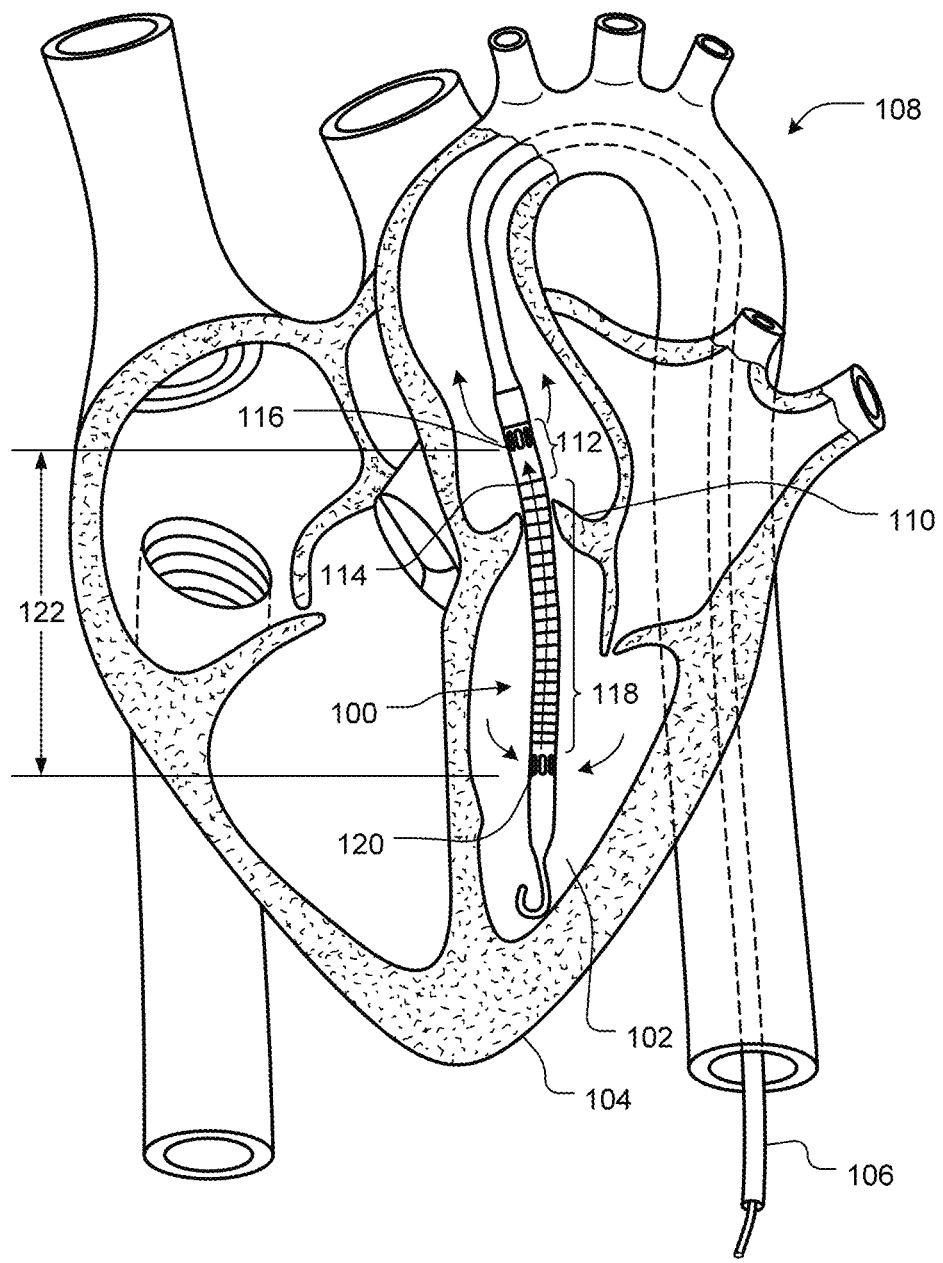
FIG. 1 shows a conventional intravascular blood pump placed in a left ventricle of a human heart, according to the prior art.

FIG. 1 shows a conventional fixed-diameter (non-expandable) intravascular blood pump 100 placed in a left ventricle 102 of a heart 104 of a human patient. The blood pump 100 is disposed at an end of a catheter 106, by which the blood pump 100 is inserted into the left ventricle 102, such as via an aorta 108. The blood pump 100 is positioned to extend through an aortic valve 110. Leaves of the aortic valve 110 close around the blood pump 100.

The blood pump 100 includes a pump housing 112, which houses an impeller and a motor (not visible). The pump housing 112 defines an axial pump housing input port 114 and a radial pump housing output port 116. The radial pump housing output port 116 may include a plurality of apertures (windows) defined circumferentially around the pump housing 112. The impeller draws blood, through the axial pump housing input port 114, into the pump housing 112, and out the radial pump housing output port 116, as indicated by arrows.

The blood pump 100 includes an inlet cannula 118, one end of which is attached in fluid communication to the axial pump housing input port 114. The opposite end of the inlet cannula 118 defines an intake port 120. The cannula intake port 120 may include a plurality of apertures (windows) defined circumferentially around the intake cannula 118. Thus, blood is drawn from the left ventricle 102, through the cannula intake port 120, into the inlet cannula 118, for delivery to the axial pump housing input port 114.

The intake port 120 and the pump housing output port 116 are spaced apart a distance 122 such that, once the blood pump 100 has been placed in the heart 104, the intake port 120 and the pump housing output port 116 are disposed on opposite sides of the aortic valve 110, and expected longitudinal shifting of the blood pump 100 is not likely to shift the intake port 120 and the pump housing output port 116 to the same side of the aortic valve 110, or to shift the pump housing output port 116 into the aortic valve 110. The distance 122 requires a relatively long inlet cannula 118, which creates relatively high hydraulic losses, as noted, particularly since the inlet cannula 116 is connected to the input (suction) end of the pump housing 112.

Any pump pushes or throws fluid out of the pump, rather than actually mechanically forcing fluid into the pump. Discharging the fluid from the pump creates a partial vacuum within the pump. Ambient pressure of fluid at the input (suction) port of the pump, such as pressure of the blood in the left ventricle 102, pushes the fluid into the pump. The effectiveness of this push depends, at least in part, on a pressure difference between the ambient pressure and the partial vacuum. A pump will not operate property without sufficient inlet pressure. Available net positive suction head (NPSHa) must be sufficient to meet the pump's net positive suction head requirement (NPSHr), otherwise the pump may cavitate. The blood pressure in the left ventricle 102 is relatively low. Therefore, the blood pump 100 is particularly sensitive to frictional losses caused by the inlet cannula 118.

Intravascular Blood Pump with Outflow Hose

FIG. 2 shows a fixed-diameter (non-expandable) intravascular blood pump 200, according to an embodiment of the present invention. The intravascular blood pump 200 is shown positioned in the left ventricle 102 of a heart 104 of a human patient. FIGS. 3*a* and 3*b* are enlarged views of a portion 202 of FIG. 2, according to two respective embodiments.

The blood pump 200 includes a catheter 204, by which the blood pump 200 is inserted into the left ventricle 102, via the aorta 108, including the descending aorta 205 and the aortic arch 206. The catheter 204 is configured for insertion into a blood vessel, such as the aorta 206, that defines an interior volume 207, through which blood flows in a blood flow direction, for example a direction indicated by an arrow 208. The catheter 204 extends to a controller (not shown), such as an Automatic Impella Controller ("AIC") available from Abiomed, Inc., Danvers, MA 01923. The controller provides a user interface for controlling and monitoring the intravascular blood pump 200.

As used herein, the term "distal" refers to a direction or location along the catheter 204 away from the controller or user, and the term "proximal" refers to a direction or location along the catheter 204 toward the controller or user.

During insertion, the intravascular blood pump 200 is positioned to extend through the aortic valve 110, as shown in FIG. 2, although in other uses the intravascular blood pump 200 may be positioned elsewhere in a patient's vasculature, not necessarily in a heart. Furthermore, although FIG. 2 depicts the intravascular blood pump 200 inserted such that the blood flow direction 208 is away from the distal end of the catheter 204, in other uses the intravascular blood pump 200 may be inserted such that the blood flow direction 208 is toward the distal end of the catheter 204. For example, the intravascular blood pump 200 may be inserted from the left atrium 209, through the mitral valve 210, into the left ventricle 102. In the use depicted in FIG. 2, leaves of the aortic valve 110 close around the blood pump 200.

The intravascular blood pump 200 includes a pump housing 211 (best seen in FIGS. 3a and 3b), which houses an impeller (not visible, but indicated by reference numeral 212). The pump housing 211 defines an axial pump housing input port 214 and a radial pump housing output port 216. The radial pump housing output port 216 may include a plurality of apertures (windows) defined circumferentially around the pump housing 211. The impeller 212 is configured, when rotating, to pump blood from the pump housing input port 214 to the pump housing output port 216. The impeller 212 draws blood, through the axial pump housing input port 214, into the pump housing 212, and out the radial pump housing output port 216, as indicated by arrows 218.

In some embodiments, an electric motor (not visible, but indicated by reference numeral 220) is disposed in or proximate the pump housing 211. The electric motor 220 is mechanically coupled to the impeller 212 and configured to rotate the impeller 212. Electric wires 222 extend from the electric motor 220, through the catheter 204, to the controller to power the electric motor 220. In other embodiments, the impeller 212 is driven by a flexible drive shaft 224 (only a portion of which is shown, in phantom) that extends through the catheter 204 to an external motor (not shown), such as a motor in the controller.

The input port 214 of the pump housing 211 includes an intake cannula 226. One end of the intake cannula 226 is attached in fluid communication to the axial pump housing input port 214. The cannula 226 extends longitudinally in an upstream direction, relative to the blood flow direction 208. The opposite end of the intake cannula 226 defines an intake port 228. The cannula intake port 228 may include a plurality of apertures (windows), represented by aperture 230, defined circumferentially around the intake cannula 226.

The intake cannula 226 is relatively short, thereby causing relatively little hydraulic loss. In some embodiments, the intake cannula 226 is about 5-60 mm long, or about 10-25 mm long. Experiments and/or simulations show that such a relatively short intake cannula 226 may increase blood flow by about 0.2 l/min or more, compared to conventional, otherwise comparable, intravascular blood pumps. Intake cannulas 226 of other suitable lengths may be used instead.

Figure 4:
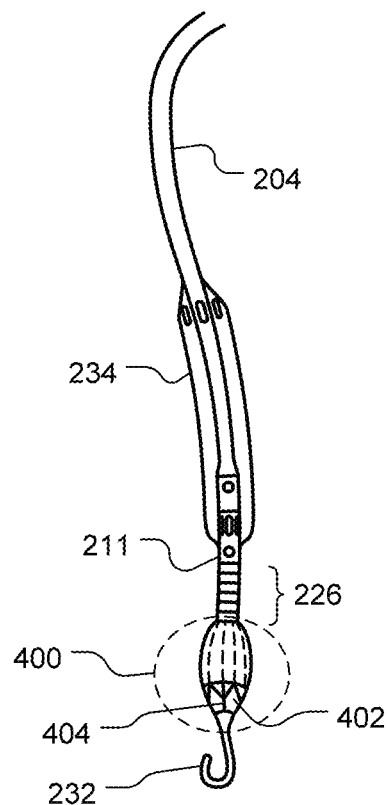
FIG. 4 shows an enlarged distal end portion of an intake cannula of the intravascular blood pump of FIG. 2, according to an alternative embodiment of the present invention.

Optionally, as shown in FIG. 4, an enlarged distal end portion 400 of the intake cannula 226 has inside and outside diameters that are larger than the remainder of intake cannula 226, and larger than the pump housing 211. The enlarged distal end portion 400 of the intake cannula 226 may define a plurality of apertures 402 circumferentially around the intake cannula 226, for example as spaces between adjacent struts, represented by strut 404.

Returning to FIG. 2, blood is drawn from the left ventricle 102, through the plurality of apertures 230, into the cannula intake port 228, through the intake cannula 226, for delivery to the axial pump housing input port 214. As discussed in more detail herein, the intake cannula 226 is much shorter, and therefore causes much less hydraulic loss, than the much longer intake cannula 118 in the prior art intravascular heart pump 100 shown in FIG. 1.

At its distal end, the intravascular blood pump 200 includes a soft pigtail or J-shaped tip 232 configured to facilitate inserting the intravascular blood pump 200 into the patient's heart 104, without harming surrounding tissue. The soft tip 232 also helps to keep soft tissue away from the blood flow inlet openings 230 of the intake cannula 226. The soft tip 232 may be, for example, about 10-60 mm long, or about 20-35 mm long.

Outflow Hose

As described thus far, the intake cannula 226, the intake port 228 and the radial pump housing output port 216 are all within the left ventricle 102. However, the intravascular blood pump 200 also includes an outflow hose 234 that extends from the radial pump housing output port 216, through the aortic valve 110, into the aorta 108. The outflow hose 234 separates where blood is discharged from the intravascular blood pump 200 from the intake port 230, i.e., a distance 236, at least as great as in the prior art, but without requiring a long intake cannula 118 (FIG. 1).

Figure 5:
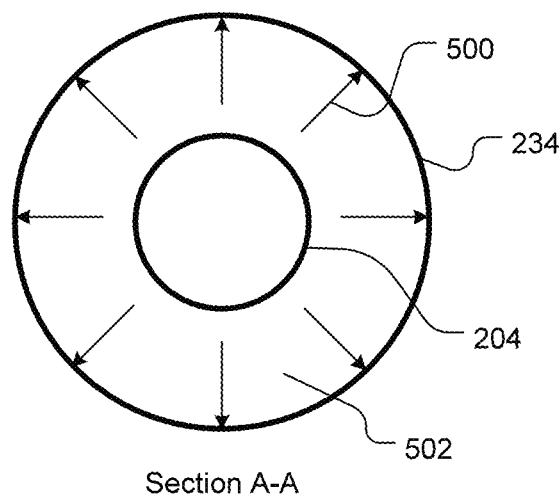
FIG. 5 is a cross-sectional view of an outflow hose and a catheter of the intravascular blood pump of FIGS. 2-4, with the outflow hose inflated, according to an embodiment of the present invention.

The outflow hose 234 may be substantially cylindrical and coaxial with the catheter 204, as shown in cross-section in FIG. 5. Alternatively, the outflow hose 234 may have another suitable cross-sectional shape (not shown). The outflow hose 234 may be disposed so as to enclose the catheter 204, as shown in FIG. 5, for the length of the outflow hose 234. Alternatively (not shown), the outflow hose 234 may extend parallel to, but not coaxial with, the catheter 204.

The outflow hose 234 is in fluid communication with the output port 216 of the pump housing 211. A proximal end 237 of the outflow hose 234 should be mechanically attached to the catheter 204, to prevent the proximal end 237 sliding along the catheter 204 into the left ventricle 102. Similarly, a distal end 304 of the outflow hose 234 should be mechanically attached to the cannula 204, to the pump housing 211 or to the intake cannula 226.

As shown in FIG. 3a, the distal end 304 of the outflow hose 234 may be more distal than the most distal portion of the apertures of the output port 216. However, this configuration may create an undesirable blood recirculation zone 306 between the distal end 304 of the outflow hose 234 and the most distal portion of the apertures of the output port 216. As shown in FIG. 3b, to avoid this potential problem, the most distal end 304 of the outflow hose 234 should be attached to the cannula 204, the pump housing 211 or the intake cannula 226 as close as practical to the most distal portion of the apertures of the output port 216.

To facilitate inserting and withdrawing the intravascular blood pump 200, an outside diameter of a portion of the outflow hose 234 near the proximal end 237 may taper along the proximal direction, i.e., in the downstream direction, radially inward. However, in other embodiments, the outside diameter of the proximal portion of the outflow hose 234 is not tapered.

Near its proximal end 237, the outflow hose 234 defines a discharge port 238, which may include a plurality of apertures defined circumferentially around the outflow hose 234. The discharge port 238 is in fluid communication with the interior volume 207 of the blood vessel (in this case, the aorta 205).

The apertures may all be defined along a single circumferential row around the outflow hose 234, as shown in FIG. 3. Alternatively, the apertures may be defined along two or more circumferential rows, as shown in FIGS. 16-19. The pump housing 211 and the output port 216 of the pump housing 211 are shown in phantom in FIG. 16. The embodiment shown in FIGS. 16-19 has three rows 1600, 1602 and 1604 of apertures; although other embodiments may have other numbers of rows, such as two, four, five, six or more rows of apertures. The rows 1600-1604 may be spaced apart longitudinally along the outflow hose 234, as exemplified by longitudinal spacing 1606. Each row 1600-1604 may contain one or more apertures.

Figure 17:
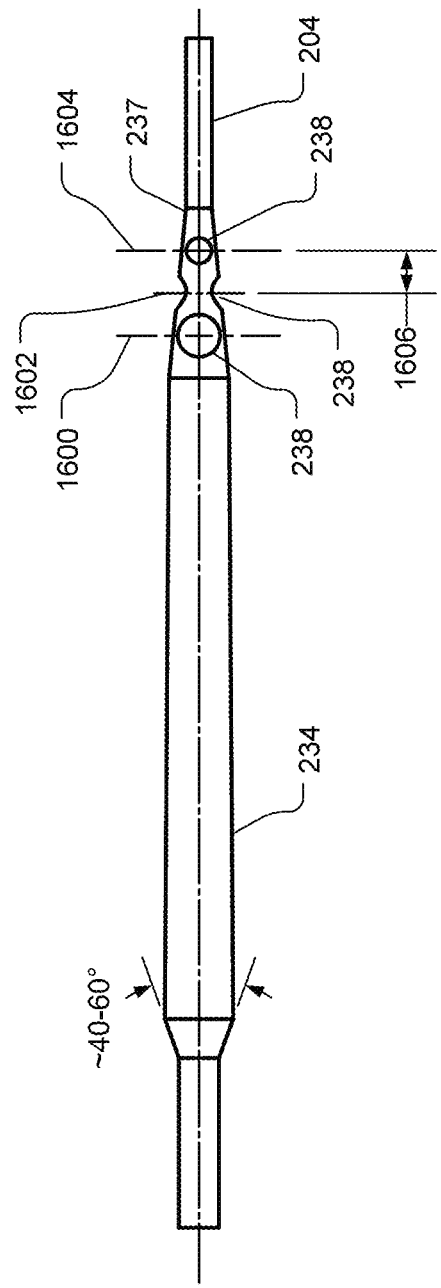
FIGS. 17 and 18 are respective side views (one rotated 90 degrees about a longitudinal axis), of an intravascular blood pump according to an alternative embodiment of the present invention.
Figure 18:
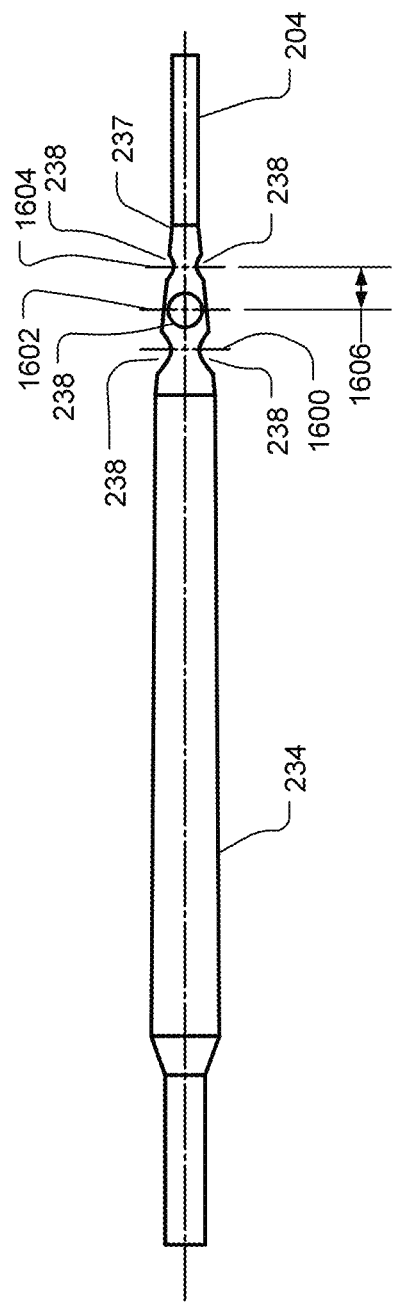
Figure 19:
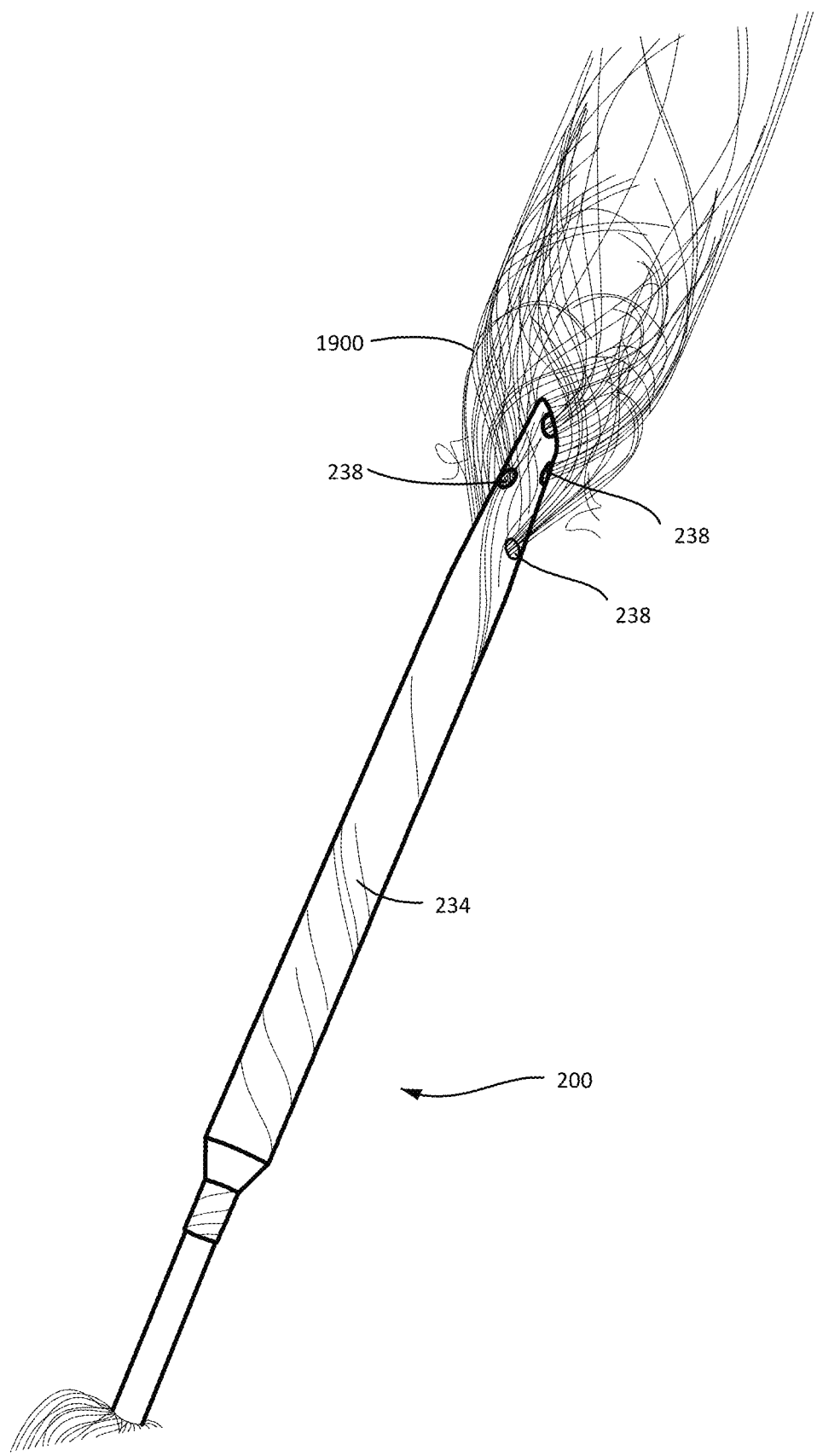
FIG. 19 illustrates exemplary blood flow from a discharge port from the intravascular blood pump of FIGS. 16-18, as simulated by a computer program.

The embodiment shown in FIGS. 16-19 has two apertures per row 1600-1604, as can most clearly be seen in FIGS. 17-18. However, other embodiments may have other numbers of apertures per row 1600-1604, such as one, three, four, five, six or more apertures per row. All the rows 1600-1604 can, but need not necessarily, have the same number of apertures. The apertures of each row 1600-1604 may be offset by an angle 1606, such as about 90° or another suitable angle, from the apertures of the adjacent row(s) 1600-1604. The multiple rows 1600-1604 of apertures, and angular offsets 1606, reduce vibration of intravascular blood pump 200 and help stabilize the intravascular blood pump 200. FIG. 19 illustrates exemplary helical blood flow 1900 from the discharge port 238, as a result of the multiple rows 1600-1603 of apertures and the angular offsets 1606, as simulated by a computer program. Advantageously, the multiple rows 1600-1603 of apertures and the angular offsets 1606 may prevent or limit blood back flow during diastole.

The discharge port 238 is longitudinally spaced apart, in a downstream direction relative to the blood flow direction 208, from the output port 216 of the pump housing 211. This longitudinal spacing is indicated by distance 240. In various embodiments, the distance 240 may be at least about 50 mm, at least about 80 mm, at least about 100 mm, about 50-150 mm, about 80-120 mm, or another distance suitable for reducing risk that the discharge port 238 and the intake port 230 are inadvertently shifted to the same side of the aortic valve 110, and/or to reduce risk that the discharge port 238 is inadvertently shifted to the aortic valve 110, even if the intravascular blood pump 200 shifts longitudinally an expected distance further into the left ventricle 102.

The distance 240 may be selected based on various considerations, such as: dimensions of an expected patient's heart chamber and/or heart valve, taking into consideration age of the patient and/or condition of the heart; dimensions of the pump housing 211 and/or dimensions of other components of the intravascular heart pump 200; and desired length of the intake cannula 226 to achieve a desired low hydraulic loss in the intake cannula 226. However, disposing the discharge port 238 too high in the aorta 108 may result in an undesirable blood flow pattern, such as flow reversal during heart ejection.

In some embodiments, the outflow hose 234 has a length of at least about 50 mm, at least about 80 mm, about 100 mm, at least about 100 mm, between about 50 and 150 mm, between about 80 and 120 mm, or another length suitable for reducing risk that the discharge port 238 and the intake port 230 are inadvertently shifted to the same side of the aortic valve 110 and/or to reduce risk that the discharge port 238 is inadvertently shifted to the aortic valve 110, even if the intravascular blood pump 200 shifts longitudinally an expected distance further into the left ventricle 102.

The length of the outflow hose 234 may be selected based on various considerations, such as: dimensions of an expected patient's heart, taking into consideration age of the patient and/or condition of the heart; dimensions of the pump housing 211 and/or dimensions of other components of the intravascular heart pump 200; and desired length of the intake cannula 226 to achieve a desired low hydraulic loss in the intake cannula 226.

The discharge port 238 is longitudinally spaced apart, in a downstream direction relative to the blood flow direction 208, from the intake port 230 of the intake cannula 226. This longitudinal spacing is indicated by the distance 236. In some embodiments, the distance 236 is at least about 90 mm. In other embodiments the distance 236 is at least about 100 mm. In yet other embodiments, the distance 236 is another distance suitable for reducing risk that the discharge port 238 and the intake port 230 are inadvertently shifted to the same side of the aortic valve 110, and/or to reduce risk that the discharge port 238 is inadvertently shifted to the aortic valve 110, even if the intravascular blood pump 200 shifts longitudinally an expected distance further into the left ventricle 102.

The distance 236 may be selected based on various considerations, such as: dimensions of an expected patient's heart chamber and/or heart valve, taking into consideration age of the patient and/or condition of the heart; dimensions of the pump housing 211 and/or dimensions of other components of the intravascular heart pump 200; and desired length of the intake cannula 226 to achieve a desired low hydraulic loss in the intake cannula 226.

Some prior art expandable intravascular heart pumps (not shown) have impellers disposed relatively close to their intake ports. Such an intravascular heart pump advantageously incurs relatively little hydraulic loss in the inlet cannula, due to the proximity of the impeller to the intake port, i.e., due to the relatively short inlet cannula. However, in this configuration, the intake port is disposed relatively close to the distal end of the catheter, near the pigtail or J-shaped tip. This position of the intake port is relatively close to an inside wall of the heart chamber. Consequently, there is a relatively high risk that the spinning impeller will draw heart tissue, such as trabeculae carneae, into the intake port and possibly damage the heart tissue. Ideally, the impeller 212 should be spaced apart from the intake port 230 by at least about 2 cm, to prevent the impeller 212 damaging ingested trabeculae carneae.

On the other hand, the prior art intravascular heart pump 100 disposes the impeller relatively far from the intake port 114, thereby advantageously reducing the risk of damage to heart tissue. However, as noted, this disposition of the impeller requires a relatively long inlet cannula 118, with its attendant relatively high hydraulic loss.

Embodiments of the present invention solve this dilemma and provide both advantages: low risk or damage to heart tissue, and low hydraulic loss.

The outflow hose 234 may be made of a suitable biocompatible material, such as a suitable polymer, such as polyurethane, polyamide, nylon or silicone. In some embodiments, the outflow hose 234 is radially collapsible, as indicated by arrows 600 in FIG. 6, and/or radially expandable, as indicated by arrows 500 in FIG. 5. In such embodiments, the outflow hose 234 may be configured to increase in radius, for example at least about 25%, or at least about 50%, or at least about 75%, or at least about 100%, or at least about 133%, or at least about 150% from an initial radius, in response to blood pressure generated by the impeller 212, when the impeller 212 pumps blood. Essentially, the blood pressure inflates the outflow hose 234. FIG. 5 shows the outflow hose 234 and the catheter 204 with the outflow hose 234 inflated. In some embodiments, the outflow hose 234 is resiliently radially collapsible and/or resiliently radially expandable. In other embodiments, the expandability and/or collapsibility of the outflow hose 234 need not be resilient. In other words, the outflow hose 234 may be "floppy" when not inflated, and the outflow hose 234 may essentially fold or wrinkle to collapse and unfold to expand. As used herein, the term "inflate" does not necessarily require stretching the material of the outflow hose 234, and "collapse" does not necessarily require the opposite of stretching the material of the outflow hose 234.

Figure 6:
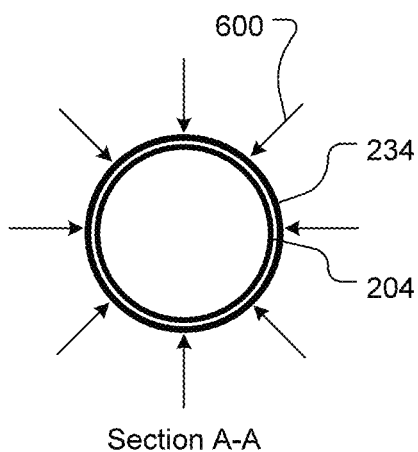
FIG. 6 is a cross-sectional view of the outflow hose and the catheter of FIG. 5, with the outflow hose deflated, according to an embodiment of the present invention.

The outflow hose 234 may be configured to radially collapse, as shown in FIG. 6, for lack of blood pressure, when the impeller 212 pumps no blood. FIG. 6 shows the outflow hose 234 and the catheter 204 with the outflow hose 234 deflated. Such a radially expandable outflow hose 234 facilitates inserting and removing the intravascular blood pump 200 by reducing outside diameter of the outflow hose 234 during the insertion and removal. For example, in some embodiments, the catheter 204 may have a size of about 9 Fr, and the outflow hose 234 may have essentially the same size (9 Fr) or slightly larger when collapsed or unexpanded, but the outflow hose 234 may have a size of about 18-21 Fr when inflated.

The outflow hose 234 has an effective inside cross-sectional area 502 (FIG. 5), which equals the inside cross-sectional area of the outflow hose 234, minus the outside cross-sectional area of the catheter 204 and outside cross-sectional area of any other structure(s) inside the outflow hose 234 that would impede blood flow between the pump housing output port 216 and the discharge port 238. In the embodiment shown in FIG. 5, the effective inside cross-sectional area 502 has an annular shape. In other embodiments, the effective inside cross-sectional area 502 may have another shape.

Figure 7:
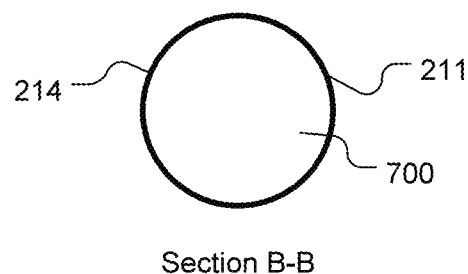
FIG. 7 is a cross-sectional view of a pump housing and an input port of the pump housing of the intravascular blood pump of FIGS. 2-4, according to an embodiment of the present invention.

The effective inside cross-sectional area 502 of the outflow hose 234 should be at least as large as the inside cross-sectional area 700 (FIG. 7) of the input port 214 of the pump housing 211. Preferably, the effective inside cross-sectional area 502 of the outflow hose 234 is greater than the inside cross-sectional area of the input port 214 of the pump housing 211. In some embodiments, the effective inside cross-sectional area 502 of the outflow hose 234 is at least twice as large as the inside cross-sectional area of the input port 214 of the pump housing 211. The effective inside cross-sectional area 502 of the outflow hose 234 should be greater than the inside cross-sectional area of the pump housing 211.

The effective inside cross-sectional area 502 of the outflow hose 234 should be at least as large as the inside cross-sectional area of the intake cannula 226. Preferably, the effective inside cross-sectional area 502 of the outflow hose 234 is greater than the inside cross-sectional area of the intake cannula 226. In some embodiments, the effective inside cross-sectional area 502 of the outflow hose 234 is at least twice as large as the inside cross-sectional area of the intake cannula 226.

Such an outflow hose 234 may yield an increase in blood flow of up to about 0.2 l/min, over a conventional otherwise comparable intravascular blood pump. For a 14F intravascular blood pump 200, i.e. an intravascular blood pump 200 having a maximum outer diameter of almost 5 mm, the total achievable blood flow under regular conditions is about 4 l/min.

Pressure Sensors

The intravascular blood pump 200 flow rate can be estimated based on dimensions of the intravascular blood pump 200 and a difference in pressure measurements taken at two or more points. To facilitate measuring these pressures, a first pressure sensor 300 (FIG. 3) may be disposed on the pump housing 211, upstream of the distal end of the outflow hose 234. Alternatively, the first pressure sensor may be disposed on or near the proximal end of the intake cannula 226, adjacent the pump housing input port 214, or elsewhere along the intake cannula 226, such as proximate the apertures 230 of the intake port 228, as indicated at 242 (FIG. 2), as long as the first pressure sensor 300 is in direct contact with the blood in the left ventricle 102, i.e., not via an interior portion of the intravascular blood pump 200. In other words, the first pressure sensor 300 should be on an outside of the intravascular blood pump 200. The first pressure sensor 300 should be disposed in a location that is unlikely to shift out of the left ventricle 102 under any likely use scenario while the intravascular blood pump 200 is in operation, so the first pressure sensor 300 can be relied upon to report pressure in the left ventricle 102. The locations described herein meet this criterion.

In the prior art, an intravascular blood pump 100 (FIG. 1) that includes an intake cannula 118 attached to a pump housing 112 is usually positioned such that the pump housing 112 is disposed across a heart valve 110. Because the intravascular blood pump 100 may shift longitudinally during use, the intake cannula 118, rather than the pump housing 112, may come to lie within the heart valve 110. It is, therefore, not appropriate for such a prior art intravascular blood pump 100 to include a pressure sensor near its pump housing 112. Such a pressure sensor could be shifted away from the left ventricle 102 and, therefore, provide incorrect pressure measurements. Therefore, in prior art intravascular blood pumps 100, the pressure sensor is typically disposed at a distal end of the intake cannula 118. Embodiments of the present invention do not suffer from this shortcoming.

A second pressure sensor 302 (FIG. 3) may be disposed inside the outflow hose 234 to measure blood pressure in the outflowing blood, as generated by the intravascular blood pump 200. The blood pressure inside the outflow hose 234 is substantially the same as the blood pressure in the aorta 205, because the blood flows from the outflow hose 234 into the aorta 205 without any substantially pressure loss. The outflow hose 234 and the discharge port 238, including the plurality of apertures defined circumferentially around the outflow hose 234, are configured to provide substantially unimpeded blood flow therethrough, so as not to cause any substantial pressure drop. Alternatively, the second pressure sensor may be disposed on the catheter 204, inside or outside the outflow hose 234. However, placement on the motor housing 211 is preferred, to facilitate connecting the second pressure sensor 302 to wires that extend through the catheter 204 to the controller. These wires transfer signals from the first and second pressure sensors 300 and 302 to the controller.

The controller may be configured to estimate the intravascular blood pump 200 flow rate from blood pressure measurements provided by the first and second pressure sensors 300 and 302, i.e., from blood pressures inside the left ventricle 102 and inside the outflow hose 234.

Blood Flow Inlet Apertures

Figure 8:
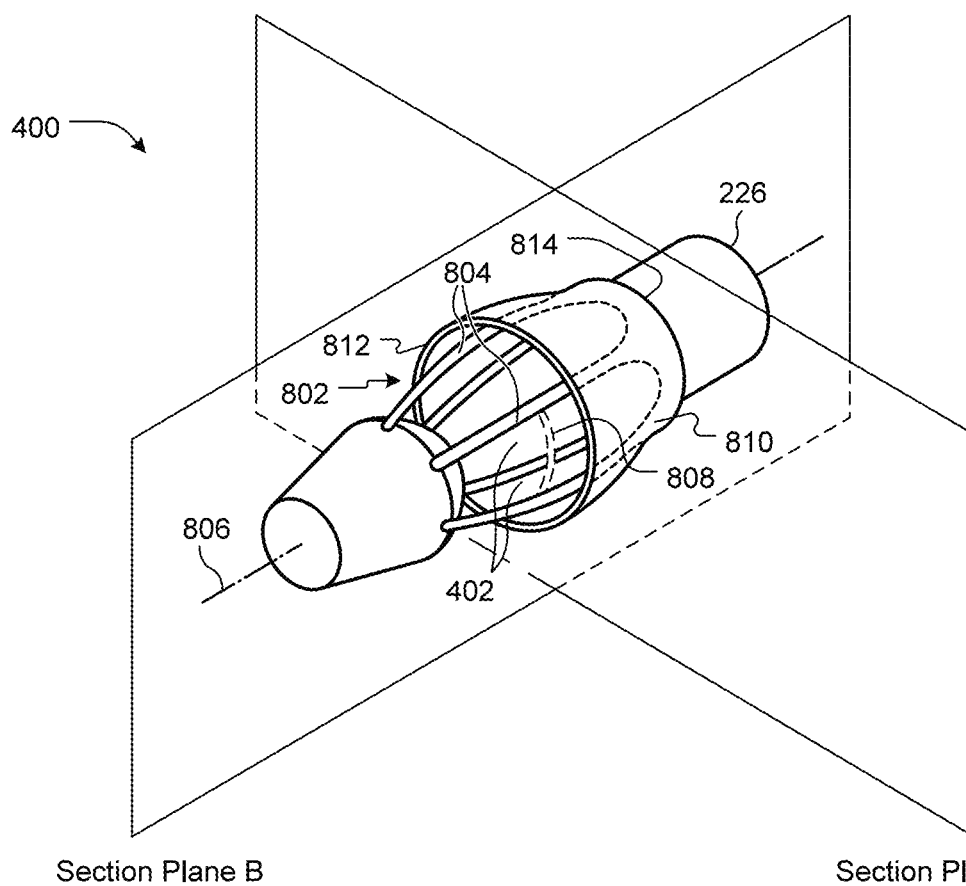
FIG. 8 is a perspective view.
Figure 9:
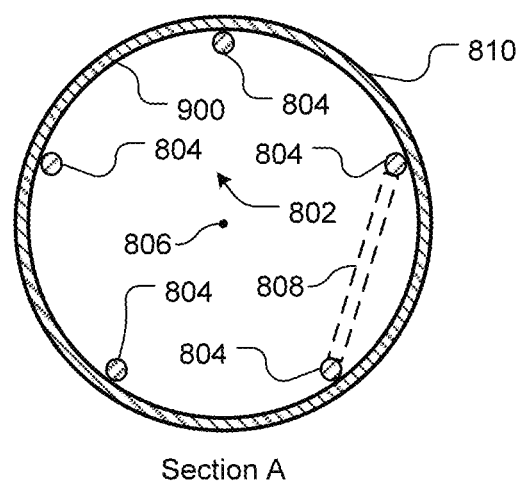
FIG. 9 is a transverse cross-sectional view and FIG. 10 is a longitudinal cross-sectional view of an end portion of the intravascular blood pump of FIGS. 2-3, according to an embodiment of the present invention.
Figure 10:
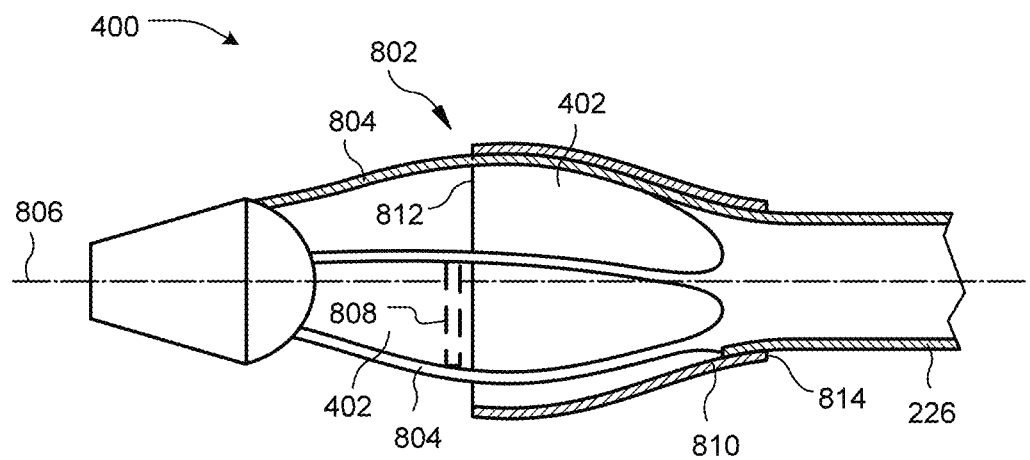

As noted, the enlarged distal end portion 400 of the intake cannula 226 may have an enlarged diameter portion 400 (FIG. 4), which defines a plurality of apertures 402. FIGS. 8-10 are respective perspective, transverse cross-sectional and longitudinal cross-sectional views of the enlarged diameter portion 400 of the intake cannula 226, according to an embodiment of the present invention. FIGS. 8-10 show the enlarged diameter portion 400 of the intake cannula 226 under normal intravascular blood pump 200 operating conditions, including typical blood pressure and flow rate of about 4 liters per minute (l/min).

The plurality of apertures 402 are defined by a frame structure, such as a cage 802 that includes struts 804. Each strut 804 separates a pair of adjacent apertures 402 from each other. In this embodiment, the struts 804 extend substantially axially parallel to the longitudinal axis 806 of the intake cannula 226. However, in other embodiments, the struts 804 may extend radially or helically, or the struts 804 may form any other suitable shape to define the apertures 402 therebetween. In the embodiment shown in FIGS. 8-10, five struts 804 form the cage 802. However, other embodiments may include more or fewer struts 804. For example, some embodiments (not shown) include three, four, six, seven, eight or more struts 804.

Optionally, in any embodiment, the struts 804 may be interconnected by members, represented by member 808 shown in phantom, extending between pairs of the struts 804. The members 808 are configured to strengthen the cage 802, so as to resist collapse or other deformation.

A sleeve 810 covers a portion of the enlarged distal end portion 400 of the intake cannula 226 to reduce likelihood of tissue suction into the apertures 402. The sleeve 810 overlaps a portion of the intake cannula 226 and extends over a proximal portion of the cage 802.

The sleeve 810 may have a funnel shape to increase the blood flow rate of the intravascular blood pump 200. The funnel shape decreases in cross-sectional diameter in a direction from a distal end 812 of the sleeve 810 toward a proximal end 814 of the sleeve 810. The sleeve 810 should monotonically narrow in cross-sectional diameter in the direction from the distal end 812 toward the proximal end 814. In particular, the cross-sectional diameter of the distal end 812 of the sleeve 810 should not decrease in the upstream direction.

As can be most clearly seen in FIG. 9, the cross-sectional shape of the sleeve 810 may be substantially circular, at least when no blood is being pumped, and the sleeve 810 may be supported by the struts 804 of the cage 802. That is, the inside wall of the sleeve 810 may contact, and be held in place radially outward, by the struts 804.

However, in some embodiments (not shown), the inside diameter of the sleeve 810 may be greater than the outside diameter of a circle that circumscribes the struts 804. Under certain conditions, the sleeve 810 may be held radially open by blood flowing into the sleeve 810. In this case, the flowing blood exerts pressure on the inside surface 900 of the sleeve 810 to maintain the funnel shape of the sleeve 810 and, therefore, prevent collapse of the sleeve 810 during operation of the intravascular blood pump 200. Optionally or alternatively, the sleeve 810 may be made of an appropriate material that is strong enough to prevent collapse of the sleeve 810, or the sleeve 810 may be reinforced by a suitable structure, as described in herein.

Figure 11:
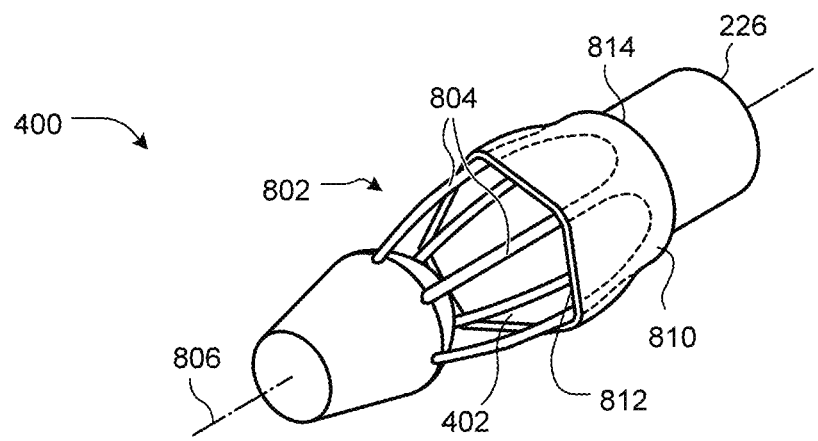
FIG. 11 is a perspective view.
Figure 12:
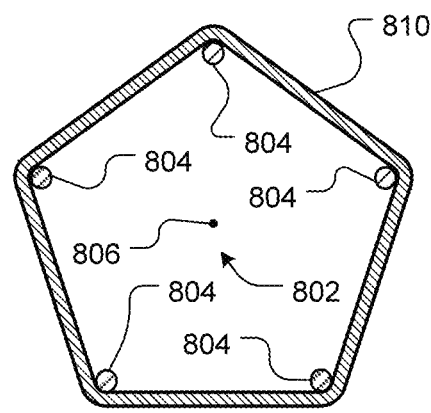
FIG. 12 is a transverse cross-sectional view, of an end portion of the intravascular blood pump of FIGS. 2-3, according to another embodiment of the present invention.
Figure 13:
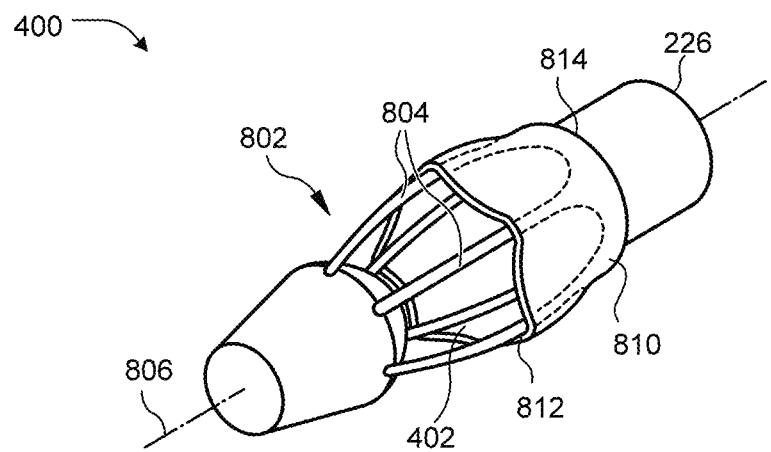
FIG. 13 is a perspective view.

In some embodiments, or under certain circumstances, the sleeve 810 may assume a cross-sectional shape other than substantially circular, for example as shown in FIGS. 11-12. The sleeve 810 may be tightly fitted around the struts 804. If, for example, the cage 802 includes five struts 804, the sleeve 810 may take on pentagonal cross-sectional shape, as shown in FIG. 12.

Figure 14:
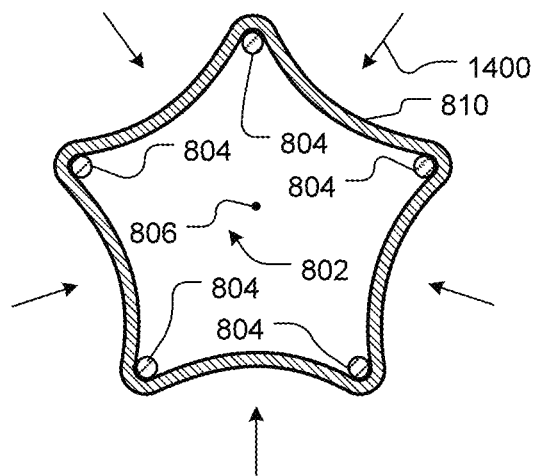
FIG. 14 is a transverse cross-sectional view, of an end portion of the intravascular blood pump of FIGS. 2-3, according to yet another embodiment of the present invention.

As a result of inward pressure, indicated by arrows 1400 (FIG. 14), exerted by the blood at the distal end 812 of the sleeve 810, the sleeve 810 may deflect inwards from the struts 804 into the apertures 402. However, the sleeve 810, struts 804, etc. should be configured so as to limit the defection to no more than about 0.2 mm at each side, radially inward, to avoid adversely affecting the blood flow under expected pressures and flow rates. In particular, the sleeve 810 should have sufficient stiffness to prevent the sleeve 810 being sucked into the apertures 402, which could possibly block the apertures 402.

Expandable Cage

Optionally, in any embodiment, the cage 802, as well as the sleeve 810 and optionally also the intake cannula 226, may be diametrically expandable. That is to say, these parts may be configured such that, before insertion into an operating position, these parts may assume a compressed configuration having a relatively small diameter, and after insertion into the operating position, these parts may be diametrically expanded to a larger diameter. In particular, in the compressed configuration (not shown), the outside diameter of the enlarged diameter portion 400 may be substantially the same as, or smaller than, the outside diameter of the remainder of the intake cannula 226 to facilitate delivery of the intravascular blood pump 200 through an introducer sheath. Then, after the intravascular blood pump 200 has been positioned for operation, the enlarged diameter portion 400 may be expanded to an outside diameter greater than the outside diameter of the remainder of the intake cannula 226, as shown in the drawings.

Although the sleeve 810 may have a structure that provides sufficient radial stiffness to prevent the sleeve 810 collapsing during normal operation of the intravascular blood pump 200, e.g. a structure that includes a membrane of an appropriate material, such as polyurethane, an additional reinforcement structure may be provided that is attached to, or embedded in, the sleeve 810. The reinforcement structure provides radial stiffness during operation of the intravascular blood pump 200, but at the same time provides expansion and compression characteristics to allow the components to be resiliently: (a) compressed to facilitate insertion of the intravascular blood pump 1; (b) expanded, once the blood pump is in position; and (c) later compressed again to facilitate removal of the intravascular blood pump 200 from the patient. In some embodiments, the intake cannula 266 is expandable to an outside diameter larger than the outside diameter of the pump housing 211, over a majority or an entirety of the axial length of the intake cannula 266. The expandable cage 802 and sleeve 810 are may be made using information provided in the aforementioned U.S. Pat. No. 8,439,859 and/or U.S. Pat. Publ. No. 2019/0046702.

Such an expandable cage 802 and sleeve 810 may yield an increase in blood flow of up to about 0.2 l/min, over a conventional otherwise comparable intravascular blood pump, without increasing risk of hemolysis. An intake cannula 226 that is expandable over a majority of its axial length may yield a further increase in blood flow of up to about 0.2 l/min, over a conventional otherwise comparable intravascular blood pump 100. An expandable pump housing, such as described in the aforementioned U.S. Pat. No. 8,439,859, may be used as an intake cannula 226 for the intravascular blood pump 200 described herein.

Alternative Intake Cannula

Figure 15:
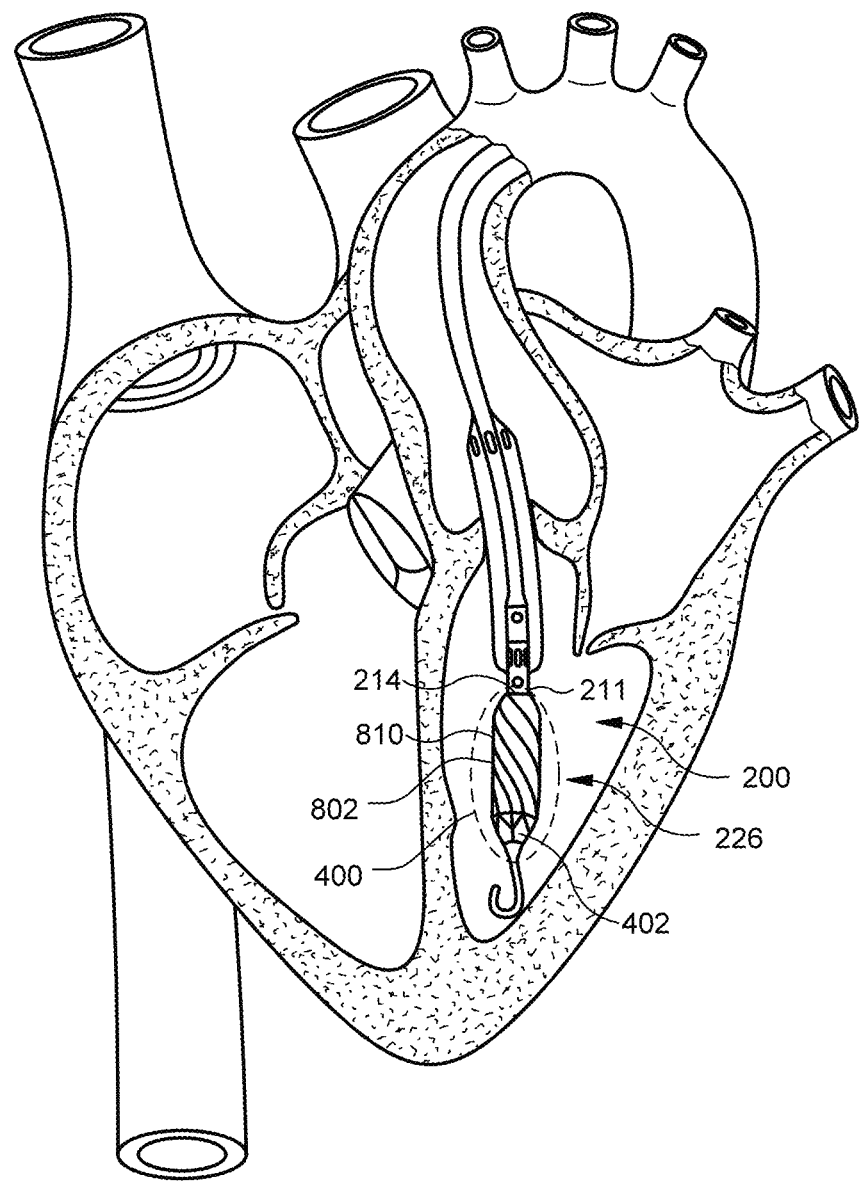
FIG. 15 shows an intravascular blood pump that includes an alternative intake cannula placed in a left ventricle of a human heart, according to another embodiment of the present invention.
Figure 16:
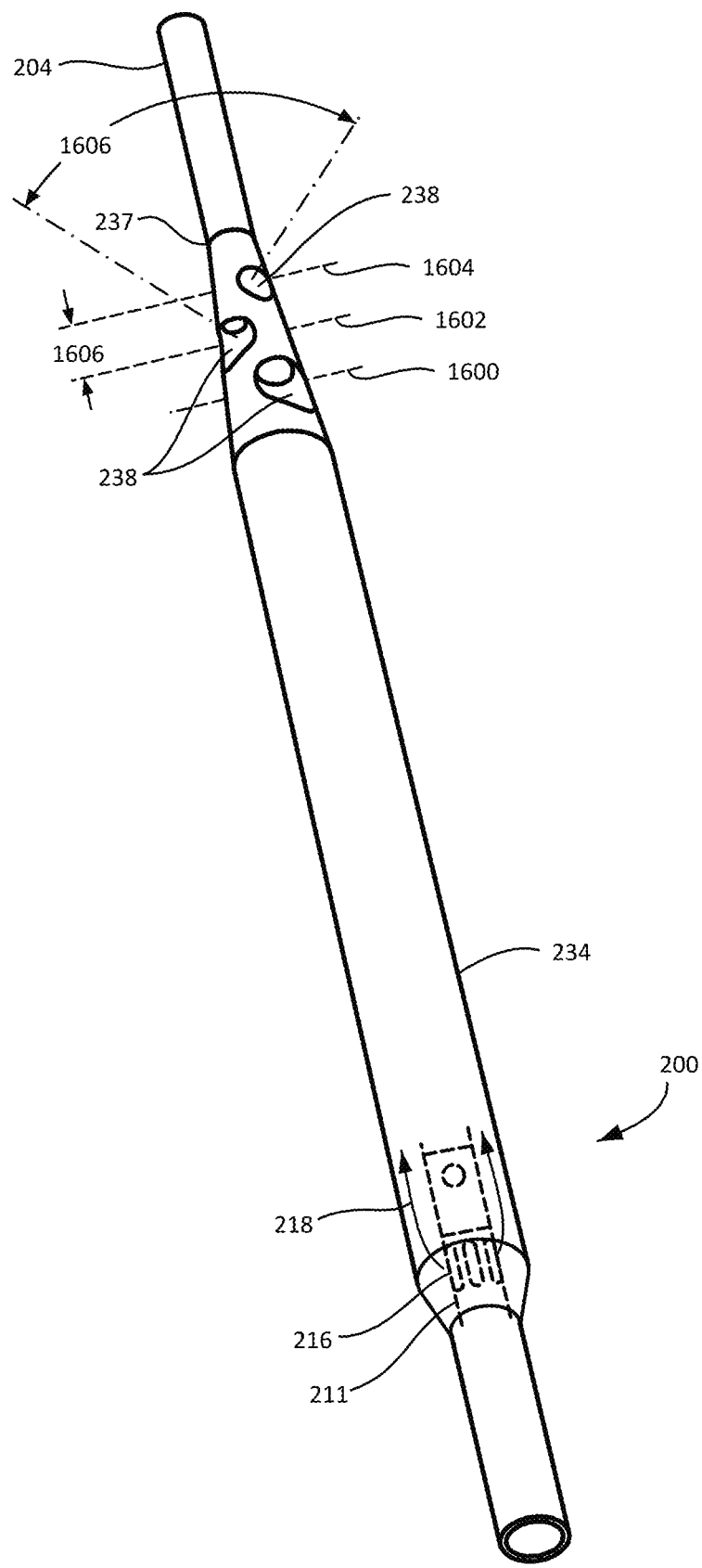
FIG. 16 is a perspective view.

FIG. 15 shows another embodiment of the blood pump 200, which differs from the embodiment described with reference to FIGS. 2-3 only in the configuration of the intake cannula 226. In the embodiment shown in FIG. 15, the enlarged diameter portion 400 of the intake cannula 226 extends over the entire length of the intake cannula 226. Thus, the apertures 402 are arranged at the distal end section of the cage structure 802. However, the remainder of the cage structure 802 is covered by the sleeve 810, and the proximal end of the cage structure 802 is attached to the input port 214 of the pump housing 211. The intake cannula 226 may be produced in the same way as the pump housing of an expandable intravascular blood pump discussed herein. For example, the cage structure 802 may be produced using well-known laser cutting techniques. Advantageously, the pump housing 211 and the cage structure 802 of the intake cannula 266 may be fabricated from a single tube, so that they form an integral piece.

The various intake cannulas 266 and apertures 402 described herein prevent, or at least reduce risk of, soft tissue, such as filaments in the left ventricle 102, being drawn into the apertures 402. Furthermore, the intake cannulas 226 described herein prevent, or at least reduce risk of, the apertures 402 being shifted out of the left ventricle 102 while the intravascular blood pump 200 is in use, even as a result of a slight longitudinal movement of the intravascular blood pump 200.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within +20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective pressure sensors or other elements from one another and are not intended to indicate any particular order or total number of pressure sensors or other elements in any particular embodiment. Thus, for example, a given embodiment may include only a second pressure sensor and a third pressure sensor.

What is claimed is:

1. An intravascular blood pump, comprising:
   a catheter configured for insertion into a blood vessel that defines an interior volume through which blood flows in a blood flow direction;
   a pump housing attached to the catheter and defining an input port and an output port;
   an impeller disposed within the pump housing and configured, when rotating, to pump blood from the input port to the output port;
   a cannula having a proximal end and a distal end, wherein the proximal end of the cannula is attached in fluid communication to the input port of the pump housing and the cannula defines an intake port that is distal of the input port of the pump housing; and
   an outflow hose having a proximal end and a distal end, the proximal end of the outflow hose attached to the catheter, the outflow hose enclosing a portion of the catheter and the output port of the pump housing, wherein the distal end of the outflow hose is in fluid the communication with the output port of the pump housing, and the intake port of the cannula is exterior to and distal of the distal end of the outflow hose, wherein the outflow hose defines a discharge port that is longitudinally spaced apart, in a downstream direction relative to the blood flow direction, from the output port of the pump housing and that is in fluid communication with the interior volume of the blood vessel.

2. An intravascular blood pump according to claim 1, wherein the outflow hose is coaxial with the catheter.

3. An intravascular blood pump according to claim 1, wherein effective inside cross-sectional area of the outflow hose is at least as large as effective inside cross-sectional area of the input port of the pump housing.

4. An intravascular blood pump according to claim 1, wherein effective inside cross-sectional area of the outflow hose is greater than effective inside cross-sectional area of the input port of the pump housing.

5. An intravascular blood pump according to claim 1, wherein effective inside cross-sectional area of the outflow hose is at least two times effective inside cross-sectional area of the input port of the pump housing.

6. An intravascular blood pump according to claim 1, wherein effective inside cross-sectional area of the outflow hose is greater than effective inside cross-sectional area of the pump housing.

7. An intravascular blood pump according to claim 1, wherein the discharge port of the outflow hose is longitudinally spaced apart, in a downstream direction relative to the blood flow direction, from the output port of the pump housing by at least about 50 mm.

8. An intravascular blood pump according to claim 1, wherein the discharge port of the outflow hose is longitudinally spaced apart, in a downstream direction relative to the blood flow direction, from the output port of the pump housing by at least about 80 mm.

9. An intravascular blood pump according to claim 1, wherein the discharge port of the outflow hose is longitudinally spaced apart, in a downstream direction relative to the blood flow direction, from the output port of the pump housing by at least about 100 mm.

10. An intravascular blood pump according to claim 1, wherein the discharge port of the outflow hose is longitudinally spaced apart, in a downstream direction relative to the blood flow direction, from the output port of the pump housing by about 50-150 mm.

11. An intravascular blood pump according to claim 1, wherein the discharge port of the outflow hose is longitudinally spaced apart, in a downstream direction relative to the blood flow direction, from the output port of the pump housing by about 80-120 mm.

12. An intravascular blood pump according to claim 1, wherein the outflow hose is at least about 50 mm long.

13. An intravascular blood pump according to claim 1, wherein the outflow hose is at least about 80 mm long.

14. An intravascular blood pump according to claim 1, wherein the outflow hose is at least about 100 mm long.

15. An intravascular blood pump according to claim 1, wherein the outflow hose is at between about 50 mm long and about 150 mm long.

16. An intravascular blood pump according to claim 1, wherein the outflow hose is at between about 80 mm long and about 120 mm long.

17. An intravascular blood pump according to claim 1, wherein the outflow hose is radially collapsible and/or radially expandable and configured to increase in radius at least about 25% from an initial radius in response to blood pressure generated by the impeller, when the impeller pumps blood, and to at least partially collapse for lack of blood pressure, when the impeller pumps no blood.

18. An intravascular blood pump according to claim 1, further comprising a first pressure sensor disposed on the pump housing, outside the outflow hose.

19. An intravascular blood pump according to claim 1, further comprising a second pressure sensor disposed inside the outflow hose.

20. An intravascular blood pump according to claim 1, wherein the output port of the pump housing comprises a plurality of apertures defined circumferentially around the pump housing.

21. An intravascular blood pump according claim 1, wherein the output port of the pump housing comprises a plurality of apertures defined along a plurality of rows, wherein the rows are spaced apart longitudinally along the outflow hose.

22. An intravascular blood pump according to claim 1, wherein the cannula extends longitudinally in an upstream direction, relative to the blood flow direction, to the intake port defined by the cannula, the intake port being in fluid communication with the interior volume of the blood vessel.

23. An intravascular blood pump according to claim 1, wherein a portion of the cannula that defines the intake port is radially expandable to a diameter larger than an outside diameter of the pump housing.

24. An intravascular blood pump according to claim 1, wherein the discharge port of the outflow hose is longitudinally spaced apart, in a downstream direction relative to the blood flow direction, from the intake port of the cannula by at least about 90 mm.

25. An intravascular blood pump according to claim 1, further comprising an electric motor disposed in the pump housing, mechanically coupled to the impeller and configured to rotate the impeller.

26. An intravascular blood pump according to claim 1, further comprising a drive shaft disposed in the catheter, mechanically coupled to the impeller and configured to transfer rotational energy to the impeller from a motor external to the intravascular blood pump.

* * * * *